United States Patent [19]

Suzuki et al.

[11] Patent Number: 5,098,919
[45] Date of Patent: Mar. 24, 1992

[54] PYRROLO(2,1-B)THIAZOLE DERIVATIVES

[75] Inventors: Norio Suzuki; Atsushi Nakayama; Toru Hosokami; Masashi Hasegawa; Shuichi Yokohama, all of Tokyo, Japan

[73] Assignee: Daiichi Pharmaceutical Co., Ltd., Tokyo, Japan

[21] Appl. No.: 552,031

[22] Filed: Jul. 13, 1990

[30] Foreign Application Priority Data

Jul. 13, 1989 [JP] Japan .................................. 1-151141

[51] Int. Cl.$^5$ .................... A61K 31/425; C07D 211/60
[52] U.S. Cl. ...................... 514/368; 548/180; 540/603; 544/581; 544/133; 544/333; 544/568; 546/148; 546/210; 514/212; 514/202; 514/233; 514/255; 514/256; 514/321; 514/378
[58] Field of Search .................... 548/180; 514/368

[56] References Cited

U.S. PATENT DOCUMENTS 4,193,926 3/1980 Schmiechen et al. .............. 560/42
4,347,186 8/1982 Muchowski et al. .............. 548/516

OTHER PUBLICATIONS

CA: 109, 2288S (1988) Lelezanet et al. J. Med. Chem. 1988 31, 1427-1429.
CA: 106, 119748x (1987) Anderson et al.: Synth-Communicate, 1986, 16, 911-915.
Chemical Abstracts vol. 110, No. 23, 5 Jun. 1989, p. 725, Abstract No. 212537v.
Yakugaku Zasshi, vol. 92, No. 4, 1972, pp. 465-470.
Chemical Abstracts vol. 86, No. 11, 14 Mar. 1977, p. 594, Abstract No. 72427t.
Journal of the American Chemical Society, vol. 66, No. 11, 1944, pp. 1883, 1884.

Primary Examiner—Nicholas S. Rizzo
Assistant Examiner—Jyothsna Venkat
Attorney, Agent, or Firm—Sughrue, Mion, Zinn, Macpeak & Seas

[57] ABSTRACT

A compound represented by the following formula (I):

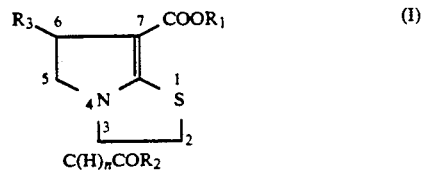

wherein $R_1$ represents a hydrogen atom, an alkyl group or a cyclic alkyl group;

$R_2$ represents a hydroxyl group, an alkoxy group which may have one to three substituents in the alkyl group moiety, an arylthio group which may have one or more substituents in the aryl group moiety, an aryloxy group which may have one or more substituents in the aryl group moiety, an amino group, an alkylamino group or a cyclic amino group which may contain other hetero atoms as ring atoms selected from a nitrogen atom, an oxygen atom and a sulfur atom;

$R_3$ represents a hydrogen atom, an alkyl group, an aryl group which may have one or more substituents, or a hetero aryl group which may have one or more substituents; m represents 1 or 2 and ═ represents a single bond or a double bond; salts thereof, and pharmaceutical preparations for preventing and treating hepatic diseases containing the compound of the formula (I) or salts thereof as an active ingredient are disclosed.

6 Claims, No Drawings

PYRROLO(2,1-B)THIAZOLE DERIVATIVES

FIELD OF THE INVENTION

This invention relates to pyrrolothiazole derivatives represented by the following formula (I):

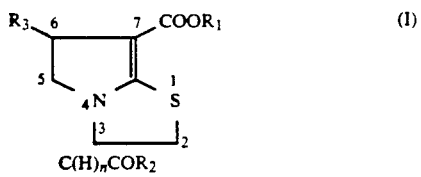

wherein $R_1$ represents a hydrogen atom, an alkyl group or a cyclic alkyl group;

$R_2$ represents a hydroxyl group, an alkoxy group which may have one to three substituents in the alkyl group moiety, an arylthio group which may have one or more substituents in the aryl group moiety, an aryloxy group which may have one or more substituents in the aryl group moiety, an amino group, an alkylamino group or a cyclic amino group which may contain one or more hetero atoms as ring atoms selected from a nitrogen atom, an oxygen atom and a sulfur atom;

$R_3$ represents a hydrogen atom, an alkyl group, an aryl group which may have one or more substituents or a hetero aryl group which may have one or more substituents; m represents 1 or 2 and represents a single bond or a double bond; salts thereof and pharmaceutical preparations for preventing or treating hepatic diseases containing the compound of the formula (I) or salts thereof as an active ingredient.

The compound of the formula (I) and salts thereof are highly effective in suppressing denaturation and necrosis of hepatocytes and improving hepatopathy. Thus they serve as excellent pharmaceutical preparations for preventing or treating hepatic diseases.

BACKGROUND OF THE INVENTION

Glycyrrhizin and interferon are frequently applied to the clinical treatment of hepatic diseases. However each of them is employed in the form of an injection which is unsuitable pharmaceutical preparation for long term treating. Therefore they are not always satisfactory from a clinical viewpoint as a treating and preventing agent for hepatic diseases.

SUMMARY OF THE INVENTION

We have conducted extensive studies in order to find a compound which is effective in suppressing denaturation and hepatocytes necrosis and improving hepatic injury and shows high safety when administered via an oral route. As a result, we have completed the present invention.

The present invention relates to a compound of the formula (I), salts thereof and pharmaceutical preparations for preventing or treating hepatic diseases containing these compounds as an active ingredient.

DETAILED DESCRIPTION OF THE INVENTION

The term "alkyl group" used herein means a straight-chain alkyl group having 1 to 10 carbon atoms and a branched-chain alkyl group having 1 to 10 carbon atoms. More particularly, examples of the straight-chain alkyl group include methyl, ethyl, n-propyl, n-butyl, pentyl, hexyl, heptyl, octyl, decyl groups and the like, and examples of the branched-chain alkyl group include isopropyl, isobutyl, sec-butyl, tert-butyl, isopentyl, 1-methylbutyl, 1,1-dimethylbutyl, 1,2-dimethylbutyl, 1,3-dimethylbutyl, 1-methylpentyl, isohexyl groups and the like.

Examples of the cyclic alkyl group include those having 3 to 8 carbon atoms (for example, cyclopropyl, cyclobutyl, cyclopentyl, cyclohexyl, cycloheptyl groups and the like).

Examples of the aryl group include phenyl, naphthyl, biphenyl groups and the like, and the aryl group may have one or more, preferably one to three substituents selected from an alkyl group, an alkoxy group, a halogen atom, a hydroxyl group, an amino group, a carboxyl group, a nitro group and a trifluoromethyl group.

Examples of the hetero aryl group include 5- to 6-membered hetero aryl group such as furyl, thienyl, oxazolyl, imidazolyl, thiazolyl, pyrrolyl, pyridyl, pyrimidyl groups and the like, and the hetero aryl group may have one or more, preferably one to three substituents selected from an alkyl group, an alkoxy group, a halogen atom, a hydroxyl group, an amino group, a carboxyl group, a nitro group and a trifluoromethyl group.

Examples of the alkoxy group include those having 1 to 10 carbon atoms (for example, methoxy, ethoxy, n-propoxy, isopropoxy, n-butoxy, tert-butoxy groups and the like). The alkoxy group for the substituent $R_2$ may have one to three substituents in the alkyl group moiety selected from a halogen atom and a hydroxyl group, and preferable examples thereof include 2,2,2-trifluoroethyl group and 2-hydroxyethyl group.

Examples of the halogen atom include fluorine, chlorine, bromine and iodine atoms.

The alkylamino group means a mono- or dialkylamino group wherein said alkyl groups may be same or different and each of them has 1 to 6 carbon atoms, and examples thereof include methylamino, ethylamino, n-propylamino, isopropylamino, n-butylamino, isobutylamino, sec-butylamino, N,N-dimethylamino, N,N-diethylamino, N-methyl-N-ethylamino groups and the like.

Examples of the cyclic amino group include three-to seven-membered cyclic amino group which may have one or more, preferably one to two hetero atoms as ring atoms selected from an oxygen atom, a sulfur atom and a nitrogen atom and examples thereof include piperidino, morpholino, thiomorpholino, pyrrolidino, piperazino, aziridino, azetidino, imidazolidino, thiazolidino, oxazolidino, pyrazolidino, homopiperidino, homopiperadino groups and the like.

Among the compounds of the present invention represented by the formula (I), those wherein $R_1$ is a branched-chain alkyl group or a cycloalkyl group and $R_2$ is an alkylamino group or a cyclic amino group which may contain one or more hetero atoms as ring atoms selected from a nitrogen atom, an oxygen atom and sulfur atom.

Particularly preferable compounds among the compounds of the present invention are those wherein $R_1$ is an isopropyl group or a cyclohexyl group, $R_2$ is a methylamino group, an ethylamino group or a morpholino group, $R_3$ is a methyl group or a hydrogen atom and the bond between the 5- and 6-positions is a double bond are preferable.

The compound of the formula (I), wherein the bond ----at C₃-position represents a double bond, has the following geometrical isomers:

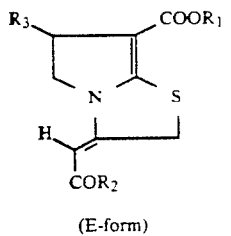

(E-form)

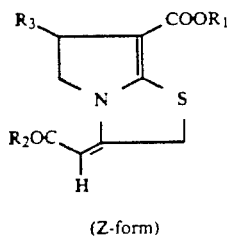

(Z-form)

The present invention includes both of these geometrical isomers as well as a mixture thereof.

In the present invention, the partial structure at C₃-position in the formula (I) is represented by the following formula as a convenient expression including the geometrical isomers.

C(H)ₙCOR₂

The compound of the formula (I) has optical isomers originating from the substituents R₁, R₂ and R₃ and the asymmetric ring carbon wherein each ----- is a single bond. These optical isomers as well as a mixture thereof are included in the present invention.

The salts of the compounds of the formula (I), particularly pharmaceutically acceptable salts thereof include acid addition salts with inorganic acids such as hydrochloric acid, sulfuric acid, nitric acid, etc., or organic acids such as fumaric acid, tartaric acid, maleic acid, succinic acid, etc., and salts involving the carboxyl group thereof, with alkali metals such as sodium, potassium, etc., or alkaline earth metals such as calcium, magnesium, etc.

Particular examples of the compound of the present invention are as follows:

ethyl (7-isopropoxycarbonyl-6-methyl-2,3,5,6-tetrahydropyrrolo[2,1-b]thiazol-3-ylidene)acetate;
ethyl (7-methoxycarbonyl-2,3,5,6-tetrahydropyrrolo[2,1-b]-thiazol-3-ylidene)acetate;
ethyl (7-ethoxycarbonyl-6-methyl-2,3,5,6-tetrahydropyrrolo[2,1-b]thiazol-3-ylidene)acetate;
ethyl (7-ethoxycarbonyl-6-isopropyl-2,3,5,6-tetrahydropyrrolo[2,1-b]thiazol-3-ylidene)acetate;
ethyl (7-isopropoxycarbonyl-6-isopropyl-2,3,5,6-tetrahydropyrrolo[2,1-b]thiazol-3-ylidene)acetate;
ethyl (7-ethoxycarbonyl-6-phenyl-2,3,5,6-tetrahydropyrrolo-[2,1-b]thiazol-3-ylidene)acetate;
ethyl (7-isopropoxycarbonyl-6-phenyl-2,3,5,6-tetrahydropyrrolo[2,1-b]thiazol-3-ylidene)acetate;
methyl (7-ethoxycarbonyl-6-methyl-2,3,5,6-tetrahydropyrrolo-[2,1-b]thiazol-3-ylidene)acetate;
ethyl (7-tert-butoxycarbonyl-2,3,5,6-tetrahydropyrrolo-[2,1-b]thiazol-3-ylidene)acetate;
ethyl (7-sec-butoxycarbonyl-2,3,5,6-tetrahydropyrrolo-[2,1-b]thiazol-3-ylidene)acetate;
4-nitrophenyl (7-isopropoxycarbonyl-6-methyl-2,3,5,6-tetrahydropryyolo[2,1-b]thiazol-3-ylidene)acetate;
S-phenyl (7-isopropoxycarbonyl-2,3,5,6-tetrahydropyrrolo-[2,1-b]thiazol-3-ylidene)thioacetate;
S-phenyl (7-isopropoxycarbonyl-6-methyl-2,3,5,6-tetrahydropyrrolo[2,1-b]thiazol-3-ylidene)thioacetate;
N-methyl-(7-isopropoxycarbonyl-6-methyl-2,3,5,6-tetrahydropyrrolo[2,1-b]thiazol-3-ylidene)acetamide;
N-methyl-(7-isopropoxycarbonyl-2,3,5,6-tetrahydropyrrolo-[2,1-b]thiazol-3-ylidene)acetamide;
N-methyl-(7-methoxycarbonyl-2,3,5,6-tetrahydropyrrolo[2,1-b]-thiazol-3-ylidene]acetamide;
N-methyl-(7-ethoxycarbonyl-2,3,5,6-tetrahydropyrrolo[2,1-b]-thiazol-3-ylidene)acetamide;
N-methyl-(7-tert-butoxycarbonyl-2,3,5,6-tetrahydropyrrolo-[2,1-b]thiazol-3-ylidene)acetamide;
N-methyl-(7-sec-butoxycarbonyl-2,3,5,6-tetrahydropyrrolo-[2,1-b]thiazol-3-ylidene)acetamide;
N-methyl-(7-cyclohexyloxycarbonyl-6-methyl-2,3,5,6-tetrahydropyrrolo[2,1-b]thiazol-3-ylidene)acetamide;
N-methyl-(7-ethoxycarbonyl-6-methyl-2,3,5,6-tetrahydropyrrolo[2,1-b]thiazol-3-ylidene)acetamide;
N-methyl-(7-ethoxycarbonyl-6-isopropyl-2,3,5,6-tetrahydropyrrolo[2,1-b]thiazol-3-ylidene)acetamide;
N-methyl-(7-isopropoxycarbonyl-6-isopropyl-2,3,5,6-tetrahydropyrrolo[2,1-b]thiazol-3-ylidene)acetamide;
N-methyl-(7-ethoxycarbonyl-6-phenyl-2,3,5,6-tetrahydropyrrolo[2,1-b]thiazol-3-ylidene)acetamide;
N-methyl-(7-isopropoxycarbonyl-6-phenyl-2,3,5,6-tetrahydropyrrolo[2,1-b]thiazol-3-ylidene)acetamide;
(7-isopropoxycarbonyl-6-methyl-2,3,5,6-tetrahydropyrrolo-[2,1-b]thiazol-3-ylidene)acetamide;
N-ethyl-(7-isopropoxycarbonyl-6-methyl-2,3,5,6-tetrahydropyrrolo[2,1-b]thiazol-3-ylidene)acetamide;
(7-isopropoxycarbonyl-2,3,5,6-tetrahydropyrrolo[2,1-b]-thiazol-3-ylidene)acetylpiperidine;
(7-isopropoxycarbonyl-2,3,5,6-tetrahydropyrrolo[2,1-b]-thiazol-3-ylidene)acetylmorpholine;
(7-isopropoxycarbonyl-2,3,5,6-tetrahydropyrrolo[2,1-b]-thiazol-3-ylidene)acetylthiomorpholine;
N,N-dimethyl-(7-isopropoxycarbonyl-2,3,5,6-tetrahydropyrrolo-[2,1-b]thiazol-3-ylidene)acetamide;
(7-isopropoxycarbonyl-6-methyl-2,3,5,6-tetrahydropyrrolo[2,1-b]thiazol-3-ylidene)acetylpiperidine;
(7-isopropoxycarbonyl-6-methyl-2,3,5,6-tetrahydropyrrolo[2,1-b]thiazol-3-ylidene)acetylmorpholine;
N,N-dimethyl-(7-isopropoxycarbonyl-6-methyl-2,3,5,6-tetrahydropyrrolo[2,1-b]thiazol-3-ylidene)acetamide;
(7-isopropoxycarbonyl-6-methyl-2,3,5,6-tetrahydropyrrolo[2,1-b]thiazol-3-ylidene)acetylthiomorpholine;
N-methyl-(7-isopropoxycarbonyl-6-methyl-2,3-dihydropyrrolo-2,1-b]thiazol-3-ylidene)acetamide;
N-methyl-(7-isopropoxycarbonyl-2,3-dihydropyrrolo[2,1-b]-thiazol-3-ylidene)acetamide;
N-methyl-(7-isopropoxycarbonyl-6-isopropyl-2,3-dihyiropyrrolo[2,1-b]thiazol-3-ylidene)acetamide;
N-methyl-(7-ethoxycarbonyl-6-methyl-2,3-dihydropyrrolo-2,1-b]thiazol-3-ylidene)acetamide;
(7-isopropoxycarbonyl-6-methyl-2,3-dihydropyrrolo[2,1-b]-thiazol-3-ylidene)acetamide;
N-ethyl-(7-isopropoxycarbonyl-6-methyl-2,3-dihydropyrrolo-[2,1-b]thiazol-3-ylidene)acetamide;

N-methyl-(7-isopropoxycarbonyl-6-phenyl-2,3-dihydropyrrolo-[2,1-b]thiazol-3-ylidene)acetamide;
(7-isopropoxycarbonyl-6-methyl-2,3-dihydropyrrolo[2,1-b]-thiazol-3-ylidene)acetylmorpholine;
(7-isopropoxycarbonyl-6-methyl-2,3-dihydropyrrolo[2,1-b]-thiazol-3-ylidene)acetylthiomorpholine;
(7-isopropoxycarbonyl-6-methyl-2,3-dihydropyrrolo[2,1-b]-thiazol-3-ylidene)acetylpiperidine;
N,N-dimethyl-(7-isopropoxycarbonyl-6-methyl-2,3-dihydropyrrolo[2,1-b]thiazol-3-ylidene)acetamide;
N-methyl-(7-cyclohexyloxycarbonyl-6-methyl-2,3-dihydropyrrolo[2,1-b]thiazol-3-ylidene)acetamide;
N-methyl-(6-ethyl-7-isopropoxycarbonyl-2,3-dihydropyrrolo-[2,1-b]thiazol-3-ylidene)acetamide;
methyl (7-isopropoxycarbonyl-6-methyl-2,3,5,6-tetrahydropyrrolo[2,1-b]thiazol-3-yl)acetate;
methyl (7-isopropoxycarbonyl-2,3,5,6-tetrahydropyrrolo-[2,1-b]thiazol-3-yl)acetate;
N-methyl-(7-isopropoxycarbonyl-6-methyl-2,3,5,6-tetrahydropyrrolo[2,1-b]thiazol-3-yl)acetamide;
N-methyl-(7-isopropoxycarbonyl-2,3,5,6-tetrahydropyrrolo-[2,1-b]thiazol-3-yl)acetamide;
N-methyl-(7-isopropoxycarbonyl-6-methyl-2,3-dihydropyrrolo-[2,1-b]thiazol-3-yl)acetamide;
N-methyl-(7-isopropoxycarbonyl-2,3-dihydropyrrolo[2,1-b]-thiazol-3-yl)acetamide;
(7-isopropoxycarbonyl-6-methyl-2,3-dihydropyrrolo[2,1-b]-thiazol-3-yl)acetylmorpholine; and
(7-isopropoxycarbonyl-6-methyl-2,3-dihydropyrrolo[2,1-b]-thiazol-3-yl)acetamide.

The compounds of the present invention represented by the formula (I) may be produced by various methods. Typical examples thereof are as follows.

PRODUCTION METHOD

Production method A: thiazole ring-closing

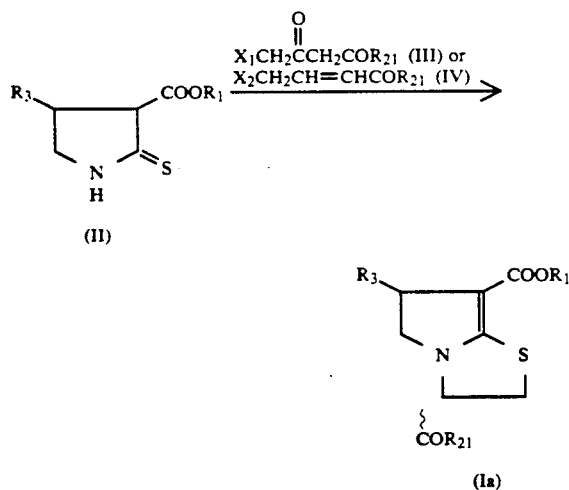

wherein $\equiv\equiv$, $R_1$ and $R_3$ are same as defined above; $R_{21}$ represents an alkoxy group which may have one or more substituents in the alkyl group moiety, an arylthio group which may have one or more substituents in the aryl group moiety or an aryloxy group which may have one or more substituents in the aryl group moiety, and $X_1$ and $X_2$ each represents a halogen atom.

The compound of formula (II) can be reacted with a compound of formula (III) or (IV) in the presence of an acid acceptor in an appropriate organic solvent to thereby produce the compound of the formula (Ia). Examples of the solvent include alcoholic solvents such as methanol, ethanol, isopropanol and the like, ethereal solvents such as tetrahydrofuran and benzene solvents such as benzene, toluene, xylene and the like. Examples of the acid acceptor include inorganic bases such as potassium carbonate and sodium carbonate, organic bases such as triethylamine, sodium acetate and potassium acetate, and the like. The reaction can be usually conducted at room temperature to 100° C. for several hours to 24 hours.

The compound of the formula (III) or (IV) can be generally used in equimolar amount as to the compound of the formula (II). Also, the acid acceptor can be used generally in equimolar amount to 3 times molar amount to the compound of the formula (II).

Production method B: amidation

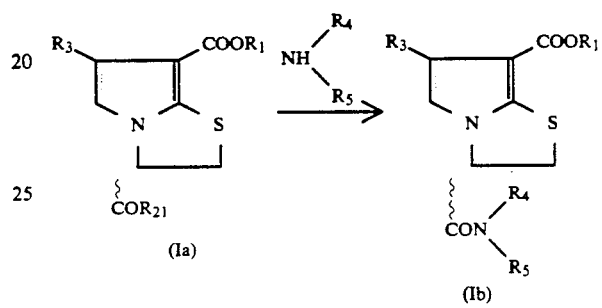

wherein $R_1$, $R_3$, $R_{21}$ and $\equiv\equiv\equiv$ are same as defined above; and $R_4$ and $R_5$ independently represents a hydrogen atom or an alkyl group, or $R_4$ and $R_5$ form a cyclic amino group together with the nitrogen atom, which may contain hetero atoms as ring atom released from a nitrogen atom, an oxygen atom and a sulfur atom.

The compound of the formula (Ia) can be reacted with $HNR_4R_5$ optionally in the presence of a metal salt such as silver salt (for example, silver trifluoroacetate and the like) or a copper salt (for example, cuprous iodide and the like) in absence of solvent or in water, organic solvent or mixture thereof to thereby produce the compound of formula (Ib). Examples of the organic solvent include an alcoholic solvent (for example, methanol, ethanol, isopropanol and the like), an ethereal solvent (for example, dioxane, tetrahydrofuran and the like), dichloromethane, chloroform, etc. The reaction can be usually carried out at 0° to 50° C. for 1 hour to 24 hours. The reaction can be preferably conducted in the presence of a metal salt at room temperature for several hours with the use of the compound of the formula (Ia) wherein $R_{21}$ is a 4-nitrophenoxy group or an arylthio group as an active ester compound.

The metal salts can be used generally in catalytic amount to the compound of the formula (Ia). The compound $NHR_4 R_5$ can be used generally in equimolar amount to in large excess amount to the compound of the formula (Ia).

Also, the compound of the formula (Ia)can be hydrolyzed with an alkali such as sodium hydroxide or potassium hydroxide in a solvent such as a mixture of water and alcoholic organic solvent, for example, methanol, ethanol, etc., at room temperature for 1 to 6 hours. The obtained hydrolizate, that is, compound of the formula (I) wherein $R_2$ represents a hydroxyl group can be reacted with a carbonic acid or an organic acid such as pivalic acid and 2,2-dimethylbutylic acid in an inert organic solvent such as dichloromethane, tetrahydrofuran, etc., at 0° C. to room temperature for several hours to several days to produce mixed acid anhydrides. Then, the mixed acid anhydrides can be reacted with HNR₄R₅ in an inert organic solvent such as tetrahydrofuran, dichloromethane, etc., to thereby give the compound of the formula (Ib). The reaction can be usually carried out at 0° C. to room temperature for several hours to several days.

The alkali can be generally used in catalytic amount to the compound of the formula (Ia). The organic acid or carbonic acid can be used generally in equimolar amount to the compound of the formula (Ia). Also, the compound HNR₄R₅ can be used generally in equimolar amount to in large excess amount to the compound of the formula (Ia).

Furthermore, the above hydrolyzate can be reacted with HNR₄R₅ in the presence of 1-hydroxybenzotriazole and N,N'-dicyclohexylcarbodiimide or N,N'-diisopropylcarbodiimide, or in the presence of 1,1'-carbonyldiimidazole in an inert organic solvent such as tetrahydrofuran, dichloromethane, etc., to thereby produce the compound of the formula (Ib). The reaction of hydrolyzate with HNR₄R₅ in the presence of 1-hydroxybenzotriazole can be preferably conducted in the presence of a catalytic amount of organic base such as 4-dimethylaminopyridine. The reaction can be usually carried out at 0° C. to room temperature for several hours to several days. The compound HNR₄R₅ can be generally used in equimolar to in large excess amount to the hydrolyzate. Also, each of 1-hydroxybenzotriazole, N,N'-dicyclohexylcarbodiimide, N,N'-diisopropylcarbodiimide, 1,1'-carbonyldiimidazole can be generally used in equimolar amount to hydrolyzate.

Production method C: dehydrogenation

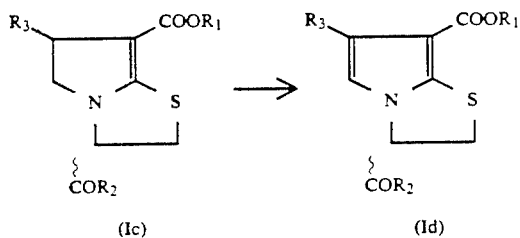

wherein R₁, R₂, R₃ and ≡≡≡≡are same as defined above.

The compound of the formula (Ic) can be reacted with a dehydrogenating agent in an appropriate solvent to thereby produce the compound of the general formula (Id). Examples of the dehydrogenating agent include palladium black, manganese dioxide, chloranil, 2,3-dichloro-5,6-dicyano-parabenzoquinone and the like. Examples of the solvent include dichloromethane, dichloroethane, chloroform, dioxane, tetrahydrofuran, mixtures thereof and the like. The reaction may be usually carried out at a temperature of from −10° to 80° C. for several hours. The reaction may be preferably conducted in a mixture of tetrahydrofuran and chloroform at room temperature for approximately 1 hour. The dehydrogenating agent can be used generally in equimolar amount to in large excess amount to the compound of the formula (Ic).

Production method D: isomerization

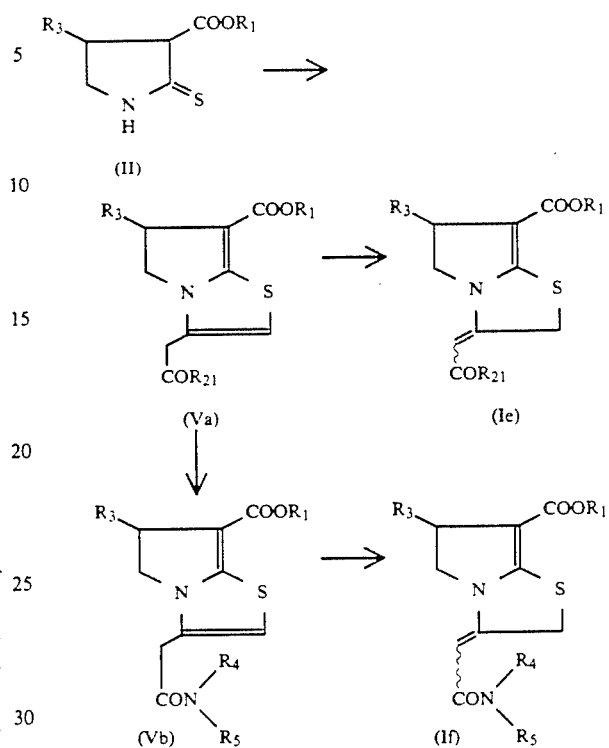

wherein R₁, R₃, R₄, R₅, R₂₁ and ≡≡≡≡are same as defined above.

The compound of the formula (II) can be reacted with the compound of formula (III) or (IV) in an organic acid such as acetic acid, propionic acid, butylic acid to thereby produce the compound of the formula (Va). The reaction may be usually conducted at room temperature to 100° C. for several hours.

The compound of the formula (Va) thus obtained can be reacted with HNR₄R₅, similar to the amidation of the production method B, to thereby produce the compound of the formula (Vb).

The compounds of formulae (Va) and (Vb) can be reacted with a base such as 1,8-diazabicyclo[5.4.0]-7-undecene in an inert organic solvent such as dichloromethane, chloroform, tetrahydrofuran, benzene or toluene to thereby produce the compounds of the formulae (Ie) and (If). The reaction can be usually carried out.

Most of the starting compound of the above formula (II) are novel compound and can be produced by appropriately combining known processes [refer to Yakugaku Zasshi, 92, 465–470 (1972); Synthesis, 138 (1982); Compt. rend., 249, 1367–1368 (1957); and Journal of American Chemical Society, 66, 1883 (1944)].

Generally, the starting compound of the formula (II) can be produced as follows.

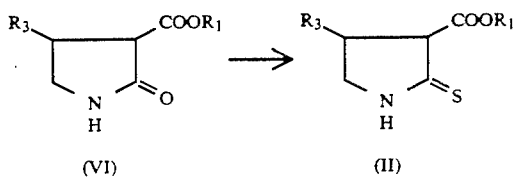

wherein, R₁, R₃ and ≡≡≡≡are same as defined above.

That is, the compound of the formula (VI) can be reacted with phosphorus pentasulfide or Lawesson's reagents in an inert organic solvent such as benzene, xylene, toluene, etc., at 50° to 60° C. for 1 to 3 hours to produce the compound of the formula (II).

The production process thereof will be described in detail in the Referential Examples hereinafter.

The compounds of the formula (I) or salts thereof can be administered either orally or parenterally, preferably orally.

The dose of the compound of the formula (I) or salts thereof may be appropriately varied depending on the age, condition and body weight of the patient. It is generally recommended to administer the compound of the formula (I) or salts thereof to an adult in a dose of from 1 to 600 mg/day, preferably from 10 to 200 mg/day. The compound of the formula (I) or salts thereof may be formulated into various dosage forms such as tablet, capsule, powders and granules together with known additives (for example, filler, lubricant, binder) by a conventional pharmaceutical techniques.

The compound of the formula (I) and salts thereof show a remarkable improving effect on an experimental hepatic injury induced by D-galactosamine in rats. Further, the compound of the formula (I) or salts thereof improves a complement-dependent hepatocyte nercrosis induced by intravenous administration of a monoclonal antibody against liver cell membrane in rats [refer to Igaku no Ayumi, 146, 3, 179–180 (1988)].

Thus the compound of the present invention is excellent as pharmaceutical preparations for preventing or treating hepatic diseases such as chronic hepatitis, acute hepatitis and hepaticcirrhosis.

To further illustrate the present invention, and not by way of limitation, the following Referential Examples, Examples and Test Examples will be given.

REFERENTIAL EXAMPLE 1

Methyl 4-Methyl-2-thioxopyrrolidine-3-carboxylate

To 4.5 g of ethyl 4-methyl-2-thioxopyrrolidine-3-carboxylate, were added 200 ml of methyl propionate and 7.0 ml of titanium tetraisopropoxide. The resulting mixture was heated under reflux for 3 days. After distilling off the excessive methyl propionate under reduced pressure, water and chloroform were added to the residue and insoluble matters were filtered off. The chloroform layer was washed with water and a saturated aqueous solution of sodium chloride and dried over anhydrous sodium sulfate. After distilling off the chloroform, ethyl ether was added to the residue to thereby crystallize the same. Thus 2.2 g of the title compound was obtained.

m.p.: 104°–105° C.

NMR spectrum δ (CDCl$_3$): 1.22 (3H, d) 2.8–3.6 (3H, m) 3.95 (3H, s) 3.7–4.1 (1H, m).

REFERENTIAL EXAMPLE 2

Isopropyl 4-Methyl-2-thioxopyrrolidine-3-carboxylate

To 5.0 g of ethyl 4-methyl-2-thioxopyrrolidine-3-carboxylate were added 300 ml of isopropyl alcohol and 11.4 g of titanium tetraisopropoxide. The resulting mixture was heated under reflux for 24 hours. After distilling off the excessive isopropyl alcohol under reduced pressure, water and chloroform were added to the residue and insoluble matters were filtered off. The chloroform layer was washed with water and a saturated aqueous solution of sodium chloride and dried over anhydrous sodium sulfate. After distilling off the chloroform, 5.0 g of the title compound was obtained.

m.p.: 41°–44° C.

NMR spectrum δ (CDCl$_3$): 1.1–1.4 (9H, m) 2.7–4.0 (4H, m) 5.11 (1H, m).

In the same manner as described in Referential Example 2, each of the following compounds of Referential Examples 3 to 5 was prepared.

REFERENTIAL EXAMPLE 3 sec-Butyl 2-Thioxopyrrolidine-3-carboxylate m.p.: 44°–45° C.

NMR spectrum δ (CDCl$_3$): 0.9–1.4 (6H, m) 1.65 (2H, m) 2.55 (2H, m) 3.5–3.9 (3H, m) 4.84 (1H, m).

REFERENTIAL EXAMPLE 4

Isopropyl 4-Isopropyl-2-thioxopyrrolidine-3-carboxylate m.p.: 90°–93° C.

NMR spectrum δ (CDCl$_3$): 0.92 (6H, d) 1.28 (3H, d) 1.34 (3H, d) 1.5–2.0 (1H, m) 2.75 (1H, q) 3.2–3.9 (3H, m) 5.13 (1H, m).

REFERENTIAL EXAMPLE 5

Isopropyl 4-Phenyl-2-thioxopyrrolidine-3-carboxylate m.p.: 97°–101° C.

NMR spectrum δ (CDCl$_3$): 1.27 (3H, d) 1.35 (3H, d) 3.6–4.3 (4H, m) 5.16 (1H, m) 7.30 (5H, s).

REFERENTIAL EXAMPLE 6

Ethyl 4-Methyl-2-thioxopyrrolidine-3-carboxylate 2.5 g of ethyl 4-methyl-2-oxopyrrolidine-3-carboxylate and 3.4 g of phosphorus pentasulfide were added to 50 ml of benzene and stirred at 50° C. for 1 hour. After cooling, the insoluble matters were filtered off and the filtrate was concentrated. The residue was purified by silica gel chromatography to thereby give 2.1 g of the title compound as an oily product.

NMR spectrum δ (CDCl$_3$): 1.23 (3H, d) 1.34 (3H, t) 2.80–4.00 (4H, m) 4.30 (2H, q).

In the same manner as described in Referential Example 6, each of the following compounds of Referential Examples 7 and 8 was prepared.

REFERENTIAL EXAMPLE 7

Ethyl 4-Isopropyl-2-thioxopyrrolidine-3-carboxylate m.p.: 68°–69° C.

NMR spectrum δ (CDCl$_3$): 0.90 (6H, d) 1.32 (3H, t) 1.75 (1H, m) 2.75 (1H, m).

REFERENTIAL EXAMPLE 8

Ethyl 4-Phenyl-2-thioxopyrrolidine-3-carboxylate m.p.: 96°–97° C.

NMR spectrum δ (CDCl$_3$): 1.32 (3H, t) 4.26 (1H, q) 4.28 (1H, q) 7.3–7.4 (5H, m).

REFERENTIAL EXAMPLE 9 tert-Butyl 2-Thioxopyrrolidine-3-carboxylate 1.7 g of tert-butyl 2-oxopyrrolidine-3-carboxylate and 1.8 g of Lawesson's reagent were added to 20 ml of benzene and stirred at 50° to 60° C. for 1 hour. After filtering the insoluble matters the solvent was distilled off and the obtained residue was purified by silica gel chromatography to thereby give 1.0 g of the title compound.

m.p.: 110°–111° C.

NMR spectrum δ (CDCl$_3$): 1.50 (9H, s) 2.3–2.7 (2H, m) 3.4–4.0 (3H, m).

EXAMPLE 1

Ethyl (7-Isopropoxycarbonyl-6-methyl-2,3,5,6-tetrahydropyrrolo[2,1-b]thiazol-3-ylidene)acetate 4.9 g of isopropyl 4-methyl-2-thioxopyrrolidine-3-carboxylate was dissolved in 50 ml of ethanol and 3.0 g of anhydrous sodium acetate and 7.7 g of 4-bromoacetoacetic acid ethyl ester were added thereto. The obtained mixture was stirred at room temperature for 3.5 hours. The crystals thus precipitated were collected by filtration, washed with water and dried. After recrystallization from a mixture of chloroform and ethanol, 3.3 g of the title compound was obtained.

m.p.: 103°–104° C.

Elemental analysis as C$_{15}$H$_{21}$NO$_4$S: calculated (%): C 57.86, H 6.80, N 4.50. found (%): C 57.92, H 6.61, N 4.36.

NMR spectrum δ (CDCl$_3$) 1.1–1.4 (12H, m) 3.1–4.0 (3H, m) 4.19 (2H, q) 4.76 (2H, d) 4.84 (1H, t) 5.07 (1H, m).

In the same manner as described in Example 1, each of the following compounds of Examples 2 to 10 was prepared.

EXAMPLE 2

Ethyl (7-Methoxycarbonyl-2,3,5,6-tetrahydropyrrolo[2,1-b]-thiazol-3-ylidene)acetate m.p.: 182°–184° C.

NMR spectrum δ (CDCl$_3$): 1.18 (3H, t) 2.9–3.2 (2H, m) 3.61 (3H, s) 3.6–3.9 (2H, m) 4.04 (2H, q) 4.80 (2H, s) 4.91 (1H, t).

EXAMPLE 3

Ethyl (7-Ethoxycarbonyl-6-methyl-2,3,5,6-tetrahydropyrrolo-[2,1-b]thiazol-3-ylidene)acetate m.p.: 148° C.

NMR spectrum δ (CDCl$_3$): 1.27 (3H, t) 1.29 (3H, t) 1.32 (3H, d) 3.20 (1H, m) 3.5–4.0 (2H, m) 4.14 (2H, q) 4.19 (2H, q) 4.77 (2H, d) 4.85 (1H, t).

EXAMPLE 4

Ethyl (7-Ethoxycarbonyl-6-isopropyl-2,3,5,6-tetrahydropyrrolo[2,1-b]thiazol-3-ylidene)acetate m.p.: 100° C.

NMR spectrum δ (CDCl$_3$): 0.78 (3H, d) 0.94 (3H, d) 1.29 (3H, t) 1.31 (3H, t) 2.35 (1H, m) 3.4–3.7 (3H, m) 4.19 (2H, q) 4.24 (2H, q) 4.82 (2H, s) 4.94 (1H, s).

EXAMPLE 5

Ethyl (7-Isopropoxycarbonyl-6-isopropyl-2,3,5,6-tetrahydropyrrolo[2,1-b]thiazol-3-ylidene)acetate m.p.: 70°–72° C.

NMR spectrum δ (CDCl$_3$): 0.75 (3H, d) 0.88 (3H, d) 1.25 (3H, t) 1.25 (6H, d) 2.1–2.6 (1H, m) 3.3–3.6 (3H, m) 4.08 (2H, q) 4.70 (2H, s) 4.82 (1H, s) 5.00 (1H, m).

EXAMPLE 6

Ethyl (7-Ethoxycarbonyl-6-phenyl-2,3,5,6-tetrahydropyrrolo-[2,1-b]thiazol-3-ylidene)acetate m.p.: 163°–164° C.

NMR spectrum δ (CDCl$_3$): 1.15 (3H, t) 1.28 (3H, t) 3.5–4.8 (7H, m) 4.90 (3H, s) 7.34 (5H, s).

EXAMPLE 7

Ethyl (7-Isopropoxycarbonyl-6-phenyl-2,3,5,6-tetrahydropyrrolo[2,1-b]thiazol-3-ylidene)acetate m.p.: 161°–163° C.

NMR spectrum δ (CDCl$_3$): 1.00 (3H, d) 1.17 (3H, d) 1.26 (3H, t) 3.58 (1H, q) 4.00 (1H, d) 4.14 (2H, q) 4.65 (1H, q) 4.85 (3H, s) 4.98 (1H, m) 7.26 (5H, s).

EXAMPLE 8

Methyl (7-Ethoxycarbonyl-6-methyl-2,3,5,6-tetrahydropyrrolo-[2,1-b]thiazol-3-ylidene)acetate m.p.: 157°–158° C.

NMR spectrum δ (CDCl$_3$): 1.31 (3H, t) 1.34 (3H, d) 3.71 (3H, s) 4.21 (2H, q) 4.80 (2H, d) 4.86 (1H, d).

EXAMPLE 9

Ethyl (7-tert-Butoxycarbonyl-2,3,5,6-tetrahydropyrrolo-[2,1-b]thiazol-3-ylidene)acetate m.p.: 178°–180° C.

NMR spectrum δ (CDCl$_3$): 1.30 (3H, t) 1.50 (9H, s) 3.0–3.3 (2H, m) 3.5–3.9 (2H, m) 4.18 (2H, q) 4.87 (3H, s).

EXAMPLE 10

Ethyl (7-sec-Butoxycarbonyl)-2,3,5,6-tetrahydropyrrolo-[2,1-b]thiazol-3-ylidene)acetate m.p.: 97°–98° C.

NMR spectrum δ (CDCl$_3$): 0.94 (3H, t) 1.26 (3H, d) 1.28 (3H, t) 1.62 (2H, m) 3.19 (2H, t) 3.69 (2H, t) 4.16 (2H, q) 4.84 (3H, m) 4.95 (1H, m).

EXAMPLE 11

4-Nitrophenyl (7-Isopropoxycarbonyl-6-methyl-2,3,5,6-tetrahydropyrrolo[2,1-b]thiazol-3-ylidene)acetate 8.9 g of isopropyl 4-methyl-2-thioxopyrrolidine-3-carboxylate was dissolved in 200 ml of benzene and 5.1 g of anhydrous sodium acetate and 16.7 g of 4-nitrophenyl 4-bromoacetoacetate were added thereto. The obtained mixture was stirred at room temperature for 8 hours. Then 500 ml of chloroform was added and the mixture was washed with water and a saturated aqueous solution of sodium chloride. After drying and distilling off the solvent, the obtained residue was purified by silica gel column chromatography. A fraction eluted with dichloromethane was crystallized from a mixture of ether and n-hexane. Thus 11.9 g of the title compound was obtained.

m.p.: 182°–183° C.

Elemental analysis as C$_{19}$H$_{20}$N$_2$O$_6$S: calculated (%): C 56.43, H 4.98, N 6.93. found (%): C 56.41, H 4.96, N 6.85.

NMR spectrum δ (CDCl₃): 1.30 (6H, d) 1.38 (3H, d) 3.2–3.4 (1H, m) 3.5–4.1 (2H, m) 4.81 (2H, s) 5.05 (1H, s) 5.10 (1H, sept) 7.30 (2H, d) 8.28 (2H, d).

EXAMPLE 12

S-Phenyl (7-Isopropoxycarbonyl-2,3,5,6-tetrahydropyrrolo-[2,1-b]thiazol-3-ylidene)thioacetate To 15 ml of 70% aqueous methanol solution which contained 470 mg of sodium hydroxide, was added 3.0 g of ethyl (7-isopropoxycarbonyl-2,3,5,6-tetrahydropyrrolo-[2,1-b]thiazol-3-ylidene)acetate. The obtained mixture was stirred at room temperature for 3 hours. The solvent was evaporated to dryness. Then 50 ml of tetrahydrofuran and 1.8 ml of triethylamine were added thereto. 1.6 ml of pivaroyl chloride was further added and the mixture was stirred for 2 hours. Subsequently 1.1 ml of thiophenol was added and the mixture was stirred at room temperature for 24 hours. Water was added to the reaction mixture followed by extracting with dichloromethane. After washing with water, the extract was dried over anhydrous sodium sulfate and distilled off. The residue was purified by silica gel column chromatography. Thus 2.6 g of the title compound was obtained as pale yellow needles.

m.p.: 216°–220° C.

Elemental analysis as $C_{18}H_{19}NO_3S_2$: calculated (%): C 59.81, H 5.30, N 3.88. found (%): C 60.00, H 5.44, N 3.97.

NMR spectrum δ (CDCl₃): 1.28 (6H, d) 3.20 (2H, t) 3.72 (2H, t) 4.78 (2H, s) 5.06 (1H, sep) 5.30 (1H, s) 7.44 (5H, s).

EXAMPLE 13

S-Phenyl (7-Isopropoxycarbonyl-6-methyl-2,3,5,6-tetrahydropyrrolo[2,1-b]thiazol-3-ylidene)thioacetate In the same manner as described in Example 12, the title compound was prepared.

m.p.: 153°–154° C.

Elemental analysis as $C_{19}H_{21}NO_3S_2$: calculated (%): C 60.77, H 5.64, N 3.73. found (%): C 60.67, H 5.70, N 3.71.

NMR spectrum δ (CDCl₃): 1.29 (6H, d) 1.35 (3H, d) 3.2–4.0 (3H, m) 4.74 (2H, d) 5.08 (1H, sep) 5.32 (1H, t) 7.44 (5H, s).

EXAMPLE 14

N-Methyl-(7-isopropoxycarbonyl-6-methyl-2,3,5,6-tetrahydropyrrolo[2,1-b]thiazol-3-ylidene)acetamide 1.2 g of ethyl (7-isopropoxycarbonyl-6-methyl-2,3,5,6-tetrahydropyrrolo[2,1-b]thiazol-3-ylidene)acetate was suspended in 25 ml of a 40% aqueous solution of monomethylamine and stirred at room temperature for 24 hours. The precipitate was collected by filtration, washed with water and recrystallized from ethanol to thereby give 1.2 g of the title compound.

m.p.: 188°–190° C.

Elemental analysis as $C_{14}H_{20}N_2O_3S$: calculated (%): C 56.74, H 6.80, N 9.45. found (%): C 56.73, H 6.60, N 9.33.

NMR spectrum δ (CDCl₃): 1.27 (6H, d) 1.31 (3H, d) 2.84 (3H, d) 3.0–3.8 (3H, m) 4.72 (1H, s) 4.86 (2H, d) 5.06 (1H, m).

EXAMPLE 15

N-Methyl-(7-isopropoxycarbonyl-6-methyl-2,3,5,6-tetrahydropyrrolo[2,1-b]thiazol-3-ylidene)acetamide 2.0 g of N-methyl-(7-isopropoxycarbonyl-6-methyl-5,6-dihydropyrrolo[2,1-b]thiazol-3-yl)acetamide was dissolved in a solvent mixture of 60 ml of chloroform and 6 ml of methanol. 0.3 g of 1,8-diazabicyclo[5.4.0]-7-undecene was added thereto and the mixture was stirred at 20° C. for 15 hours. The reaction mixture was then washed with 20 ml of 5% aqueous acetic acid, a 0.5% aqueous solution of sodium hydrogencarbonate and a saturated aqueous solution of sodium chloride. The chloroform layer was dried over anhydrous sodium sulfate. After distilling off the chloroform, the obtained crude crystals were recrystallized from ethanol to thereby give 1.5 g of the title compound.

EXAMPLE 16

N-Methyl-(7-isopropoxycarbonyl-2,3,5,6-tetrahydropyrrolo-[2,1-b]thiazol-3-ylidene)acetamide In the same manner as described in Example 14, each of the following compounds of Examples 16 to 28 was prepared.

m.p.: 197°–198° C.

Elemental analysis as $C_{13}H_{18}N_2O_3S$: calculated (%): C 55.30, H 6.43, N 9.92. found (%): C 55.63, H 6.65, N 10.07.

NMR spectrum δ (CDCl₃): 1.29 (6H, d) 2.87 (3H, d) 3.20 (2H, t) 3.66 (2H, t) 4.76 (1H, s) 4.96 (2H, s) 5.10 (1H, m).

The compound thus obtained is represented by the following structural formula:

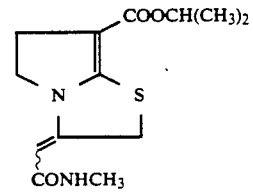

The nuclear Overhauser effect (hereinafter called NOE) of the hydrogen atom at the 2'- or 5-position in the above formula was examined in deuterated chloroform. As a result, irradiation of the hydrogen atom at the 2'-position gave a 7.5% NOE enhancement of the hydrogen atom at the 5-position while the latter gave a 11.7% NOE enhancement of the former.

EXAMPLE 17

N-Methyl-(7-methoxycarbonyl-2,3,5,6-tetrahydropyrrolo[2,1-b]-thiazol-3-ylidene)acetamide m.p.: 211°–214° C.

Elemental analysis as $C_{11}H_{14}NO_3S$: calculated (%): C 51.95, H 5.55, N 11.02. found (%): C 52.08, H 5.80, N 10.98.

NMR spectrum δ (CDCl₃): 2.59 (3H, d) 3.03 (2H, t) 3.59 (3H, s) 3.65 (2H, t) 4.79 (2H, bs) 4.95 (1H, t).

EXAMPLE 18

N-Methyl-(7-ethoxycarbonyl-2,3,5,6-tetrahydropyrrolo[2,1-b]-thiazol-3-ylidene)acetamide m.p.: 208°–209° C.

Elemental analysis as $C_{12}H_{16}N_2O_3S$: calculated (%): C 53.71, H 6.01, N 10.44. found (%): C 53.96, H 6.17, N 10.30.

NMR spectrum δ (CDCl$_3$): 1.29 (3H, t) 2.84 (3H, d) 3.18 (2H, t) 3.64 (2H, t) 4.20 (2H, q) 4.73 (1H, s) 4.90 (2H, s).

EXAMPLE 19

N-Methyl-(7-tert-butoxycarbonyl-2,3,5,6-tetrahydropyrrolo-[2,1-b]thiazol-3-ylidene)acetamide m.p.: 200°–203° C.

Elemental analysis as $C_{14}H_{20}N_2O_3S$: calculated (%): C 56.71, H 6.80, N 9.49. found (%): C 56.65, H 6.86, N 9.40.

NMR spectrum δ (CDCl$_3$): 1.50 (9H, s) 2.83 (3H, d) 3.0–3.3 (2H, m) 3.5–3.8 (2H, m) 4.70 (1H, t) 4.87 (2H, d).

EXAMPLE 20

N-Methyl-(7-sec-butoxycaronyl-2,3,5,6-tetrahydropyrrolo-[2,1-b]thiazol-3-ylidene)acetamide m.p.: 187°–188° C.

Elemental analysis as $C_{14}H_{20}N_2O_3S.5H_2O$: calculated (%): C 55.06, H 6.93, N 9.17. found (%): C 55.00, H 6.76, N 9.20.

NMR spectrum δ (CDCl$_3$): 0.93 (3H, t) 1.23 (3H, d) 1.60 (2H, m) 2.83 (3H, d) 3.17 (2H, t) 3.62 (2H, t) 4.72 (1H, br) 4.89 (2H, br) 4.91 (1H, m).

EXAMPLE 21

N-Methyl-(7-cyclohexyloxycarbonyl-6-methyl-2,3,5,6-tetrahydropyrrolo[2,1-b]thiazol-3-ylidene)acetamide m.p.: 178°–180° C.

Elemental analysis as $C_{17}H_{24}N_2O_3S$: calculated (%): C 60.69, H 7.19, N 8.33. found (%): C 60.62, H 7.19, N 8.22.

NMR spectrum δ (CDCl$_3$): 1.1–2.1 (13H, m) 2.85 (3H, d) 2.1–2.3 (1H, m) 2.4–3.0 (2H, m) 4.75 (1H, s) 4.87 (2H, s) 4.8–5.0 (1H, m).

EXAMPLE 22

N-Methyl-(7-ethoxycarbonyl-6-methyl-2,3,5,6-tetrahydropyrrolo[2,1-b]thiazol-3-ylidene)acetamide m.p.: 186°–188° C.

Elemental analysis as $C_{13}H_{18}N_2O_3S$: calculated (%): C 55.30, H 6.43, N 9.92. found (%): C 55.36, H 6.46, N 9.44.

NMR spectrum δ (CDCl$_3$): 1.29 (3H, t) 1.32 (3H, d) 2.84 (3H, d) 3.1–3.9 (3H, m) 4.19 (2H, q) 4.73 (2H, s) 4.86 (2H, s).

EXAMPLE 23

N-Methyl-(7-ethoxycarbonyl-6-isopropyl-2,3,5,6-tetrahydropyrrolo[2,1-b]thiazol-3-ylidene)acetamide:

m.p.: 180°–182° C.

Elemental analysis as $C_{15}H_{22}N_2O_3S.0.2H_2O$: calculated (%): C 57.37, H 7.19, N 8.92. found (%): C 57.60, H 7.30, N 8.82.

NMR spectrum δ (CDCl$_3$): 0.80 (3H, d) 0.94 (3H, d) 1.32 (3H, t) 2.36 (1H, m) 2.89 (3H, d) 3.3–3.7 (3H, m) 4.23 (2H, q) 4.83 (1H, s) 4.92 (2H, s).

EXAMPLE 24

N-Methyl-(7-isopropoxycarbonyl-6-isopropyl-2,3,5,6-tetrahydropyrrolo[2,1-b]thiazol-3-ylidene)acetamide m.p.: 149°–153° C.

Elemental analysis as $C_{16}H_{24}N_2O_3S$: calculated (%): C 59.23, H 7.46, N 8.63. found (%): C 59.05, H 7.22, N 8.41.

NMR spectrum δ (CDCl$_3$): 0.77 (3H, d) 0.90 (3H, d) 1.27 (6H, d) 2.1–2.6 (1H, m) 2.80 (3H, d) 3.2–3.6 (3H, m) 4.80 (3H, s) 4.98 (1H, m).

EXAMPLE 25

N-Methyl-(7-ethoxycarbonyl-6-phenyl-2,3,5,6-tetrahydropyrrolo[2,1-b]thiazol-3-ylidene)acetamide m.p.: 168°–171° C.

Elemental analysis as $C_{18}H_{20}N_2O_3S$: calculated (%): C 62.77, H 5.85, N 8.13. found (%): C 62.77, H 5.94, N 7.86.

NMR spectrum δ (CDCl$_3$): 1.13 (3H, t) 2.83 (3H, d) 3.4–5.8 (6H, m) 4.92 (2H, s) 7.26 (5H, s).

EXAMPLE 26

N-Methyl-(7-isopropoxycarbonyl-6-phenyl-2,3,5,6-tetrahydropyrrolo[2,1-b]thiazol-3-ylidene)acetamide m.p.: 143°–146° C.

Elemental analysis as $C_{19}H_{22}N_2O_3S$: calculated (%): C 63.66, H 6.19, N 7.81. found (%): C 63.52, H 6.32, N 7.95.

NMR spectrum δ (CDCl$_3$): 1.01 (3H, d) 1.17 (3H, d) 2.81 (3H, d) 3.50 (1H, q) 3.98 (1H, t) 4.5–5.1 (2H, m) 4.73 (1H, s) 4.90 (2H, d) 7.1–7.4 (5H, m).

EXAMPLE 27

(7-Isopropoxycarbonyl-6-methyl-2,3,5,6-tetrahydropyrrolo-[2,1-b]thiazol-3-ylidene)acetamide m.p.: 204°–207° C.

Elemental analysis as $C_{13}H_{18}N_2O_3S$: calculated (%): C 55.30, H 6.43, N 9.92. found (%): C 55.35, H 6.52, N 9.95.

NMR spectrum δ (CDCl$_3$): 1.28 (6H, d) 1.32 (3H, d) 3.0–3.3 (1H, m) 3.4–3.9 (2H, m) 4.82 (2H, s) 4.90 (1H, s) 5.02 (1H, m).

EXAMPLE 28

N-Ethyl-(7-isopropoxycarbonyl-6-methyl-2,3,5,6-tetrahydropyrrolo[2,1-b]thiazol-3-ylidene)acetamide m.p.: 116°–119° C.

Elemental analysis as $C_{15}H_{22}N_2O_3S$: calculated (%): C 58.04, H 7.14, N 9.02. found (%): C 58.17, H 7.32, N 8.76.

NMR spectrum δ (CDCl$_3$): 1.15 (3H, t) 1.27 (6H, d) 1.31 (3H, d) 3.1–4.0 (5H, m) 4.72 (1H, t) 4.85 (2H, d) 5.05 (1H, m).

EXAMPLE 29

(7-Isopropoxycarbonyl-2,3,5,6-tetrahydropyrrolo[2,1-b]-thiazol-3-ylidene)acetylpiperidine 1.0 g of S-phenyl (7-isopropoxycarbonyl-2,3,5,6-tetrahydropyrrolo[2,1-b]thiazol-3-ylidene)thioacetate and 1.2 g of piperidine were suspended in 40 ml of tetrahydrofuran and 740 mg of silver trifluoroacetate was added thereto under stirring at room temperature. After 2 hours, the insoluble matters were filtered off and the filtrate was concentrated. The residue was purified by silica gel column chromatography and recrystallized from ethanol. Thus 0.65 g of the title compound was obtained.

m.p.: 128°–130° C.

Elemental analysis as $C_{17}H_{24}N_2O_3S$: calculated (%): C 60.68, H 7.19, N 8.33. found (%): C 60.39, H 7.30, N 8.26.

NMR spectrum δ ($CDCl_3$): 1.29 (6H, d) 1.65 (6H, m) 3.18 (2H, t) 3.50 (4H, m) 3.68 (2H, t) 4.90 (2H, s) 5.09 (1H, sep) 5.13 (1H, s).

In the same manner as described in Example 29, each of the following compounds of Examples 30 and 31 was prepared.

EXAMPLE 30

(7-Isopropoxycarbonyl-2,3,5,6-tetrahydropyrrolo[2,1-b]-thiazol-3-ylidene)acetylmorpholine m.p.: 186°–187° C.

Elemental analysis as $C_{16}H_{22}N_2O_4S$: calculated (%): C 56.78, H 6.55, N 8.28. found (%): C 56.48, H 6.57, N 8.14.

NMR spectrum δ ($CDCl_3$): 1.28 (6H, d) 3.19 (2H, t) 3.5–3.8 (10H, m) 4.91 (2H, s) 5.06 (1H, s) 5.07 (1H, sep).

EXAMPLE 31

(7-Isopropoxycarbonyl-2,3,5,6-tetrahydropyrrolo[2,1-b]-thiazol-3-ylidene)acetylthiomorpholine m.p.: 183°–185° C.

Elemental analysis as $C_{16}H_{22}N_2O_3S_2$: calculated (%): C 54.21, H 6.26, N 7.90. found (%): C 53.97, H 6.28, N 7.74.

NMR spectrum δ ($CDCl_3$): 1.29 (6H, d) 2.66 (4H, t) 3.22 (2H, t) 3.72 (2H, t) 3.88 (4H, t) 4.94 (2H, s) 5.08 (1H, sep) 5.10 (1H, s).

EXAMPLE 32

N,N-Dimethyl-(7-isopropoxycarbonyl-2,3,5,6-tetrahydropyrrolo-[2,1-b]thiazol-3-ylidene)acetamide 1.0 g of S-phenyl (7-isopropoxycarbonyl-2,3,5,6-tetrahydropyrrolo[2,1-b]thiazol-3-ylidene)thioacetate was suspended in 10 ml of a 40% aqueous solution of dimethylamine and stirred at room temperature for 1 hour. After distilling off the excessive dimethylamine, the obtained crude crystals were recrystallized from isopropyl alcohol. Thus 0.7 g of the title compound was obtained as crystals.

m.p.: 159°–160° C.

Elemental analysis as $C_{14}H_{20}N_2O_3S \cdot 0.6H_2O$: calculated (%): C 54.73, H 6.90, N 9.12. found (%): C 54.80, H 7.05, N 8.95.

NMR spectrum δ ($CDCl_3$): 1.30 (6H, d) 3.06 (6H, s) 3.21 (2H, t) 3.72 (2H, t) 4.95 (2H, s) 5.11 (1H, sep) 5.13 (1H, s).

In the same manner as described in Example 32, each of the following compounds of Examples 33 and 34 was prepared.

EXAMPLE 33

(7-Isopropoxycarbonyl-6-methyl-2,3,5,6-tetrahydropyrrolo-[2,1-b]thiazol-3-ylidene)acetylpiperidine m.p.: 155°–158° C.

Elemental analysis as $C_{18}H_{26}N_2O_3S$: calculated (%): C 61.69, H 7.48, N 7.99. found (%): C 61.56, H 7.44, N 7.80.

NMR spectrum δ ($CDCl_3$): 1.27 (6H, d) 1.33 (3H, d) 2.5–2.8 (6H, m) 3.2–3.8 (7H, m) 4.85 (2H, d) 5.06 (1H, sep) 5.13 (1H, t).

EXAMPLE 34

(7-Isopropoxycarbonyl-6-methyl-2,3,5,6-tetrahydropyrrolo-[2,1-b]thiazol-3-ylidene)acetylmorpholine m.p.: 138°–140° C.

Elemental analysis as $C_{17}H_{24}N_2O_4S$: calculated (%): C 57.93, H 6.86, N 7.95. found (%): C 57.76, H 6.90, N 7.80.

NMR spectrum δ ($CDCl_3$): 1.27 (6H, d) 1.33 (3H, d) 3.1–3.4 (1H, m) 3.4–3.9 (10H, m) 4.85 (2H, d) 5.05 (1H, t) 5.13 (1H, sep).

EXAMPLE 35

N,N-Dimethyl-(7-isopropoxycarbonyl-6-methyl-2,3,5,6-tetrahydropyrrolo[2,1-b]thiazol-3-ylidene)acetamide To 1.50 g of 4-nitrophenyl (7-isopropoxycarbonyl-6-methyl-2,3,5,6-tetrahydropyrrolo[2,1-b]thiazol-3-ylidene)acetate, was added 40 ml of a 25% aqueous solution of dimethylamine and the mixture was stirred at room temperature for 3 days. 40 ml of water was added thereto and the precipitate thus formed was collected by filtration, washed with water and dissolved in chloroform. After drying and distilling off the solvent, the crude crystals thus obtained were recrystallized from a solvent mixture of ether and n-hexane. Thus 0.6 g of the title compound was obtained.

m.p.: 126°–128° C.

Elemental analysis as $C_{15}H_{22}N_2O_3S$: calculated (%): C 58.04, H 7.14, N 9.02. found (%): C 58.28, H 7.15, N 9.08.

NMR spectrum δ ($CDCl_3$): 1.24 (6H, d) 1.33 (3H, d) 3.02 (6H, s) 3.1–3.3 (1H, m) 3.5–3.9 (2H, m) 4.85 (2H, d) 5.08 (1H, sep) 5.10 (1H, t).

EXAMPLE 36

(7-Isopropoxycarbonyl-6-methyl-2,3,5,6-tetrahydropyrrolo-[2,1-b]thiazol-3-ylidene)acetylthiomorpholine In the same manner as described in Example 35, the title compound was prepared.

m.p.: 164°–165° C.

Elemental analysis as $C_{17}H_{24}N_2O_3S_2$: calculated (%): C 55.41, H 6.56, N 7.60. found (%): C 55.23, H 6.56, N 7.38.

NMR spectrum δ ($CDCl_3$): 1.27 (6H, d) 1.33 (3H, d) 2.5–2.8 (4H, m) 3.21 (1H, dd) 3.6–4.0 (6H, m) 4.85 (2H, d) 5.07 (1H, s) 5.13 (1H, sep).

EXAMPLE 37

N-Methyl-(7-isopropoxycarbonyl-6-methyl-2,3-dihydropyrrolo-[2,1-b]thiazol-3-ylidene)acetamide 15.3 g of N-methyl-(7-isopropoxycarbonyl-6-methyl-2,3,5,6-tetrahydropyrrolo[2,1-b]thiazol-3-ylidene)acetamide was dissolved in a solvent mixture comprising 300 ml of chloroform and 120 ml of tetrahydrofuran. Then 11.7 g of 2,3-dichloro-5,6-dicyano-parabenzoquinone was added thereto under stirring and cooling with cold water. After 0.5 hour, a saturated aqueous solution of sodium hydrogencarbonate was added thereto. After stirring, the insoluble matters were filtered off with the use of celite and the filtrate was extracted with chloroform. The chloroform phase was washed with water and a saturated aqueous solution of sodium chloride and dried. After distilling off the solvent, the obtained crude crystals were recrystallized from ethanol. Thus 12.5 g of the title compound was obtained.

m.p.: 173°–175° C.

Elemental analysis as $C_{14}H_{18}N_2O_3S$: calculated (%): C 57.12, H 6.16, N 9.52. found (%): C 57.06, H 6.12, N 9.48.

NMR spectrum δ (CDCl$_3$): 1.35 (6H, d) 2.27 (3H, s) 2.90 (3H, d) 4.91 (2H, d) 5.16 (1H, m) 5.6 (1H, m) 5.68 (1H, t) 6.67 (1H, s).

The compound thus obtained is represented by the following structural formula:

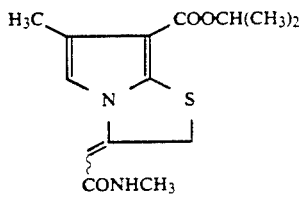

The NOE of the hydrogen atom at the 2'- or 5-position in the above formula was examined in dimethylsulfoxide (DMSO-d$^6$). As a result, irradiation of the hydrogen atom at the 2'-position gave a 10% NOE enhancement of the hydrogen atom at the 5-position while the latter gave a 6% NOE enhancement of the former.

In the same manner as described in Example 37, each of the following compounds of Examples 38 to 49 was prepared.

EXAMPLE 38

N-Methyl-(7-isopropoxycarbonyl-2,3-dihydropyrrolo[2,1-b]-thiazol-3-ylidene)acetamide m.p.: 191°–192° C.

Elemental analysis as $C_{13}H_{16}N_2O_3S$: calculated (%): C 55.70, H 5.75, N 9.99. found (%): C 55.67, H 5.86, N 10.00.

NMR spectrum δ (CDCl$_3$): 1.33 (6H, d) 2.89 (3H, d) 4.98 (2H, d) 5.15 (1H, m) 5.60 (1H, d) 5.76 (1H, t) 6.73 (1H, d) 6.86 (1H, d).

EXAMPLE 39

N-Methyl-(7-isopropoxycarbonyl-6-isopropyl-2,3-dihydropyrrolo[2,1-b]thiazol-3-ylidene)acetamide m.p.: 175°–177° C.

Elemental analysis as $C_{16}H_{22}N_2O_3S$: calculated (%): C 59.62, H 6.56, N 8.70. found (%): C 59.50, H 6.62, N 8.83.

NMR spectrum δ (CDCl$_3$): 1.20 (6H, d) 1.33 (6H, d) 2.87 (3H, d) 3.32 (1H, m) 4.85 (2H, d) 5.10 (1H, m) 5.68 (1H, t) 6.60 (1H, s).

EXAMPLE 40

N-Methyl-(7-isopropoxycarbonyl-6-phenyl-2,3-dihydropyrrolo-[2,1-b]thiazol-3-ylidene)acetamide m.p.: 155°–159° C.

Elemental analysis as $C_{19}H_{20}N_2O_3S$: calculated (%): C 64.00, H 5.66, N 7.86. found (%): C 63.79, H 5.64, N 7.90.

NMR spectrum δ (CDCl$_3$): 1.26 (6H, d) 2.88 (3H, d) 4.92 (2H, d) 5.18 (1H, m) 5.75 (1H, t) 6.85 (1H, s) 7.3–7.7 (5H, m).

EXAMPLE 41

N-Methyl-(7-ethoxycarbonyl-6-methyl-2,3-dihydropyrrolo-[2,1-b]thiazol-3-ylidene)acetamide m.p.: 177°–178° C.

Elemental analysis as $C_{13}H_{16}N_2O_3S$: calculated (%): C 55.69, H 5.75, N 9.99. found (%): C 55.37, H 5.73, N 9.94.

NMR spectrum δ (CDCl$_3$): 1.31 (3H, t) 2.22 (3H, d) 4.22 (2H, q) 4.84 (2H, d) 5.88 (1H, t) 6.72 (1H, d) 7.10 (1H, s).

EXAMPLE 42

(7-Isopropoxycarbonyl-6-methyl-2,3-dihydropyrrolo[2,1-b]-thiazol-3-ylidene)acetamide m.p.: 179°–180° C.

Elemental analysis as $C_{13}H_{16}N_2O_3S$: calculated (%): C 55.70, H 5.75, N 9.99. found (%): C 55.73, H 5.71, N 10.06.

NMR spectrum δ (CDCl$_3$): 1.27 (6H, d) 2.20 (3H, d) 4.82 (2H, d) 5.01 (1H, m) 6.04 (1H, t) 6.97 (1H, q).

EXAMPLE 43

N-Ethyl-(7-isopropoxycarbonyl-6-methyl-2,3-dihydropyrrolo-[2,1-b]thiazol-3-ylidene)acetamide m.p.: 139°–140° C.

Elemental analysis as $C_{15}H_{20}N_2O_3S$: calculated (%): C 58.42, H 6.54, N 9.08. found (%): C 58.25, H 6.33, N 9.25.

NMR spectrum δ (CDCl$_3$): 1.15 (3H, t) 1.27 (6H, d) 2.28 (3H, s) 3.1–3.6 (2H, m) 4.90 (2H, d) 5.15 (1H, m) 5.68 (1H, t) 6.65 (1H, s).

EXAMPLE 44

(7-Isopropoxycarbonyl-6-methyl-2,3-dihydropyrrolo[2,1-b]thiazol-3-ylidene)acetylmorpholine m.p.: 156°–158° C.

Elemental analysis as $C_{17}H_{22}N_2O_4S$: calculated (%): C 58.27, H 6.33, N 7.99. found (%): C 58.45, H 6.32, N 7.90.

NMR spectrum δ (CDCl$_3$): 1.33 (6H, d) 2.28 (3H, d) 3.4–3.9 (8H, m) 4.87 (2H, d) 5.15 (1H, sep) 6.06 (1H, t) 6.74 (1H, bs).

EXAMPLE 45

(7-Isopropoxycarbonyl-6-methyl-2,3-dihydropyrrolo[2,1-b]thiazol-3-ylidene)acetylthiomorpholine m.p.: 149°–155° C.

Elemental analysis as $C_{17}H_{22}N_2O_3S_2$: calculated (%): C 55.71, H 6.05, N 7.64. found (%): C 55.55, H 5.99, N 7.48.

NMR spectrum δ (CDCl$_3$): 1.33 (6H, d) 2.28 (3H, d) 2.6–2.8 (4H, m) 3.7–4.1 (4H, m) 4.86 (2H, d) 5.18 (1H, sep) 6.06 (1H, t) 6.77 (1H, d).

EXAMPLE 46

(7-Isopropoxycarbonyl-6-methyl-2,3-dihydropyrrolo[2,1-b]thiazol-3-ylidene)acetylpiperidine m.p.: 122°–123° C.

Elemental analysis as $C_{18}H_{24}N_2O_3S$: calculated (%): C 62.04, H 6.94, N 8.04. found (%): C 61.80, H 6.98, N 7.88.

NMR spectrum δ (CDCl$_3$): 1.33 (6H, d) 1.5–1.8 (6H, m) 2.28 (3H, d) 3.4–3.7 (4H, m) 4.87 (2H, d) 5.15 (1H, sep) 6.13 (1H, t) 6.76 (1H, d).

EXAMPLE 47

N,N-Dimethyl-(7-isopropoxycarbonyl-6-methyl-2,3-dihydropyrrolo[2,1-b]thiazol-3-ylidene)acetamide m.p.: 132°–135° C.

Elemental analysis as $C_{15}H_{20}N_2O_3S$: calculated (%): C 58.40, H 6.54, N 9.09. found (%): C 58.37, H 6.50, N 8.96.

NMR spectrum δ (CDCl$_3$): 1.33 (6H, d) 2.29 (3H, d) 3.07 (6H, s) 4.88 (2H, d) 5.15 (1H, sep) 6.10 (1H, t) 6.75 (1H, d).

EXAMPLE 48

N-Methyl-(7-cyclohexyloxycarbonyl-6-methyl-2,3-dihydropyrrolo[2,1-b]thiazol-3-ylidene)acetamide m.p.: 179°–181° C.

Elemental analysis as $C_{17}H_{22}N_2O_3S$: calculated (%): C 61.05, H 6.63, N 8.38. found (%): C 61.02, H 6.68, N 8.20.

NMR spectrum δ (CDCl$_3$): 1.1–2.2 (10H, m) 2.27 (3H, d) 2.89 (3H, d) 4.91 (2H, d) 4.9–5.1 (1H, m) 5.69 (1H, t) 6.65 (1H, q).

EXAMPLE 49

N-Methyl-(6-ethyl-7-isopropoxycarbonyl-2,3-dihydropyrrolo-[2,1-b]-thiazol-3-ylidene)acetamide m.p.: 179°–182° C.

Elemental analysis as $C_{15}H_{20}N_2O_3S$: calculated (%): C 58.42, H 6.54, N 9.08. found (%): C 58.41, H 6.49, N 9.12.

NMR spectrum δ (CDCl$_3$): 1.19 (3H, t) 1.33 (6H, d) 2.73 (2H, q) 2.89 (3H, d) 4.90 (2H, d) 5.15 (1H, sep) 5.71 (1H, t) 6.60 (1H, s).

EXAMPLE 50

Methyl (7-Isopropoxycarbonyl-6-methyl-2,3,5,6-tetrahydropyrrolo[2,1-b]thiazol-3-yl)acetate 4.0 g of isopropyl 4-methyl-2-thioxopyrrolidene-3-carboxylate, 4.7 g of methyl 4-bromocrotonate and 2.1 g of anhydrous sodium acetate were suspended in 100 ml of ethanol and stirred at 60° to 70° C. for 3 hours. After distilling off the solvent under reduced pressure, the residue was dissolved in ethyl acetate, washed with a saturated aqueous solution of sodium chloride and dried over anhydrous sodium sulfate. After distilling off the solvent, the obtained oily product was purified by silica gel column chromatography. Thus 4.5 g of the title compound was obtained in the form of a pale yellow oily product.

NMR spectrum δ (CDCl$_3$): 1.1–1.3 (3H, m) 1.25 (6H, d) 2.2–3.8 (8H, m) 3.72 (3H, s) 5.03 (1H, sep).

EXAMPLE 51

Methyl (7-Isopropoxycarbonyl-2,3,5,6-tetrahydropyrrolo-[2,1-b]thiazol-3-yl)acetate In the same manner as described in Example 50, the title compound was prepared.

Elemental analysis as $C_{13}H_{19}NO_4S$: calculated (%): C 54.72, H 6.71, N 4.91. found (%): C 54.71, H 6.64, N 4.74.

NMR spectrum δ (CDCl$_3$): 1.25 (6H, d) 2.5–3.8 (9H, m) 3.72 (3H, s) 5.03 (1H, sep).

EXAMPLE 52

N-Methyl-(7-isopropoxycarbonyl-6-methyl-2,3,5,6-tetrahydropyrrolo[2,1-b]thiazol-3-yl)acetamide To 4.5 g of methyl (7-isopropoxycarbonyl-6-methyl-2,3,5,6-tetrahydropyrrolo[2,1-b]thiazol-3-yl-)acetate was added 100 ml of a 40% aqueous solution of monomethylamine. The mixture was stirred at room temperature for 20 hours. After distilling off the monomethylamine, the residue was extracted with chloroform. The chloroform layer was washed with a saturated aqueous solution of sodium chloride and dried over anhydrous sodium sulfate. After distilling off the solvent, 4.1 g of the title compound was obtained in the form of a colorless oily product.

Mass spectrum m/Z: 298 (M+).

NMR spectrum δ (CDCl$_3$): 1.25 (9H, d) 1.8–3.9 (8H, m) 2.81 (3H, d) 5.01 (1H, sep).

EXAMPLE 53

N-Methyl-(7-isopropoxycarbonyl-2,3,5,6-tetrahydropyrrolo-[2,1-b]thiazol-3-yl)acetamide In the same manner as described in Example 52, the title compound was prepared.

m.p.: 79°–95° C.

Elemental analysis as $C_{13}H_{20}N_2O_3S$: calculated (%): C 54.91, H 7.09, N 9.85. found (%): C 54.86, H 7.05, N 9.91.

NMR spectrum δ (CDCl$_3$): 1.25 (6H, d) 2.3–3.8 (9H, m) 2.81 (3H, d) 5.00 (1H, sep).

EXAMPLE 54

N-Methyl-(7-isopropoxycarbonyl-6-methyl-2,3-dihydropyrrolo[2,1-b]thiazol-3-yl)acetamide 4.1 g of N-methyl-(7-isopropoxycarbonyl-6-methyl-2,3,5,6-tetrahydropyrrolo[2,1-b]-thiazol-3-yl)acetamide was dissolved in 150 ml of chloroform and 3.9 g of 2,3-dicyano-5,6-dichloro-parabenzoquinone was added thereto under ice-cooling and stirring. The mixture was stirred at room temperature for 1 hour. After removing the insoluble matters, the chloroform layer was successively washed with a saturated aqueous solution of sodium hydrogencarbonate and a saturated aqueous solution of sodium chloride. After drying over anhydrous sodium sulfate and distilling off the solvent, the obtained residue was purified by silica gel column chromatography. Thus 2.0 g of the title compound was obtained.

m.p.: 108°–109° C.

Elemental analysis as $C_{14}H_{20}N_2O_3S$: calculated (%): C 56.73, H 6.80, N 9.45. found (%): C 56.71, H 6.83, N 9.49.

NMR spectrum δ (CDCl$_3$): 1.30 (6H, d) 2.18 (3H, d) 2.3–2.7 (2H, m) 2.80 (3H, d) 3.32 (1H, dd) 3.89 (1H, dd) 4.7–5.0 (1H, m) 5.08 (1H, m) 6.38 (1H, d).

EXAMPLE 55

N-Methyl-(7-isopropoxycarbonyl-2,3-dihydropyrrolo[2,1-b]-thiazol-3-yl)acetamide

In the same manner as described in Example 54, the title compound was prepared.

m.p.: 117°–119° C.

Elemental analysis as $C_{13}H_{18}N_2O_3S$: calculated (%): C 55.30, H 6.43, N 9.92. found (%): C 55.27, H 6.38, N 9.86.

NMR spectrum δ (CDCl₃): 1.30 (6H, d) 2.57 (1H, s) 2.64 (1H, s) 2.80 (3H, d) 3.38 (1H, dd) 3.99 (1H, dd) 4.93 (1H, ddt) 5.10 (1H, sep) 6.53 (1H, d) 6.56 (1H, d).

EXAMPLE 56

(7-Isopropoxycarbonyl-6-methyl-2,3-dihydropyrrolo[2,1-b]-thiazol-3-yl)acetylmorpholine 1.54 g of (7-isopropoxycarbonyl-6-methyl-2,3-dihydropyrrolo[2,1-b]thiazol-3-yl)acetic acid, 0.70 g of morpholine and 0.12 g of 4-N,N-dimethylaminopyridine were dissolved in 50 ml of dichloromethane. 1.44 g of N,N'-dicyclohexylcarbodiimide was added thereto under ice-cooling and stirring. Then the mixture was stirred at room temperature for 9 days. After filtering off the insoluble matters, the solvent was distilled off. The oily residue thus obtained was purified by silica gel column chromatography. After crystallizing from ether/n-hexane, 1.05 g of the title compound was obtained.

m.p.: 97°–99° C.

Elemental analysis as $C_{17}H_{24}N_2O_4S$: calculated (%): C 57.93, H 6.86, N 7.95. found (%): C 57.99, H 6.91, N 7.90.

NMR spectrum δ (CDCl₃): 1.32 (6H, d) 2.22 (3H, s) 2.5–2.8 (2H, m) 3.2–3.5 (3H, m) 3.4–3.7 (6H, m) 4.00 (1H, dd) 4.7–5.1 (1H, m) 5.13 (1H, sep) 6.42 (1H, s).

EXAMPLE 57

(7-Isopropoxycarbonyl-6-methyl-2,3-dihydropyrrolo[2,1-b]-thiazol-3-yl)acetamide 1.0 g of methyl (7-isopropoxycarbonyl-6-methyl-2,3-dihydropyrrolo[2,1-b]thiazol-3-yl)acetate was dissolved in 30 ml of methanol and 30 ml of concentrated aqueous ammonia was added thereto. The obtained mixture was stirred at room temperature for 6 days. After distilling off the ammonia, the residue was extracted with chloroform. The chloroform layer was washed with a saturated aqueous solution of sodium chloride and dried over anhydrous sodium sulfate. After distilling off the solvent, the obtained oily residue was crystallized from ether/n-hexane. Thus 0.3 g of the title compound was obtained.

m.p.: 143°–146° C.

Elemental analysis as $C_{13}H_{18}N_2O_3S$: calculated (%): C 55.30, H 6.43, N 9.92. found (%): C 55.20, H 6.47, N 9.71.

NMR spectrum δ (CDCl₃): 1.31 (6H, d) 2.21 (3H, d) 2.6–2.8 (2H, m) 3.34 (1H, dd) 3.94 (1H, dd) 4.7–5.0 (1H, m) 5.12 (1H, sep) 6.43 (1H, d).

EXAMPLE 58

1) Ethyl (7-Isopropoxycarbonyl-6-methyl-5,6-dihydropyrrolo-[2,1-b]thiazol-3-yl)acetate 2.0 g of isopropyl 4-methyl-2-thioxopyrrolidene-3-carboxylate was dissolved in 30 ml of acetic acid and 4.2 g of ethyl 4-bromoacetoacetate was added thereto. The mixture was stirred at 20° C. for 1 hour. After distilling off the acetic acid under reduced pressure, 50 ml of water and chloroform were added and the aqueous layer was collected. The aqueous layer was made alkaline with sodium hydrogen-carbonate, extracted with chloroform, washed with water and dried over anhydrous sodium sulfate. After distilling off the chloroform, 1.5 g of the title compound was obtained in the form of an oily product.

NMR spectrum δ (CDCl₃): 1.26 (6H, d) 1.28 (3H, t) 1.30 (3H, d) 3.37 (2H, s) 3.3–3.8 (2H, m) 3.9–4.2 (1H, m) 4.19 (2H, q) 5.06 (1H, m) 5.86 (1H, s).

2) N-Methyl-(7-isopropoxycarbonyl-6-methyl-5,6-dihydropyrrolo[2,1-b]thiazol-3-yl)acetamide 3.3 g of ethyl (7-isopropoxycarbonyl-6-methyl-5,6-dihydropyrrolo[2,1-b]thiazol-3-yl)acetate was added to 60 ml of a 40% aqueous solution of monomethylamine and stirred at 20° C. for 24 hours. The precipitate was collected by filtration, washed with water, dried, and recrystallized from ethanol. Thus 2.2 g of the title compound was obtained.

m.p.: 203°–205° C.

Elemental analysis as $C_{14}H_{20}N_2O_3S$: calculated (%): C 56.71, H 6.80, N 9.49. found (%): C 57.03, H 6.95, N 9.65.

NMR spectrum δ (CDCl₃): 1.23 (6H, d) 1.27 (3H, d) 2.71 (3H, d) 3.30 (2H, s) 3.4–3.8 (2H, m) 4.17 (1H, m) 4.96 (1H, m) 5.92 (1H, s).

3) N-Methyl-(7-isopropoxycarbonyl-6-methyl-2,3,5,6-tetrahydropyrrolo[2,1-b]thiazol-3-ylidene)acetamide 2.0 g of N-methyl-(7-isopropoxycarbonyl-6-methyl-5,6-dihydropyrrolo[2,1-b]thiazol-3-ylidene)acetamide was dissolved in 60 ml of chloroform and 0.3 ml of 1,8-diazabicyclo[5.4.0]-7-undecene was added thereto. The obtained mixture was stirred at room temperature overnight. Then the chloroform phase was successively washed with 20 ml of a 5% aqueous solution of acetic acid and 10 ml of water. The chloroform phase was successively washed with a saturated aqueous solution of sodium hydrogencarbonate and a saturated aqueous solution of sodium chloride and dried over sodium sulfate anhydride. After distilling off the solvent, the obtained crude crystals were recrystallized from ethanol. Thus 1.2 g of the title compound was obtained.

The compound thus obtained completely identical with the one of Example 14 in m.p. and various spectrometric data.

TEST EXAMPLE 1

Effect on hepatitis model induced by D-galactosamine

Test animal

Male SD rats weighing 170 to 200 g were used

Administration of test compound

Each test compound was suspended in a 1% aqueous solution of methyl cellulose and orally administered at a dose of 400 mg/kg 1 hour before the induction of hepatic injury.

Induction of galactosamine-topathy (hepatitis)

D-galactosamine hydrochloride at 800 mg/kg was administered (subcutaneously) to rats to induce hepatitis. The animals were fasted after the administration of D-galactosamine. After 24 hours, the blood samples were collected from the vena cava under etherization and serum GPT and GOT were measured as indices of hepatic injury.

Results

Table 1 shows the results.

TABLE 1

|  | GPT U/L | GOT U/L |
| --- | --- | --- |
| Normal control group (n = 6) | 39 ± 5 | 93 ± 11 |
| Disease control group (n = 6) | 1961 ± 333 | 1652 ± 265 |
| Test group (n = 6) | | |
| Compound of Ex. 16 | 437 ± 58** | 496 ± 43** |
| Compound of Ex. 37 | 338 ± 36** | 483 ± 45** |

**p < 0.05 (to disease control group).

Table 1 clearly shows the values of serum GPT and GOT in the test group were significantly lower than those in the disease control group. Thus the compound of the present invention is proved to be highly effective in improving or preventing hepatitis induced by administration of D-galactosamine hydrochloride.

TEST EXAMPLE 2

The compound of the Example 16 or 37 suspended in a 1% aqueous solution of methyl cellulose was orally administered to male SD rats at a dose of 400 mg/kg. As a result, no animal died.

While the invention has been described in detail and with reference to specific embodiments thereof, it will be apparent to one skilled in the art that various changes and modifications can be made therein without departing from the spirit and scope thereof.

What is claimed is:

1. A compound represented by the following formula (I):

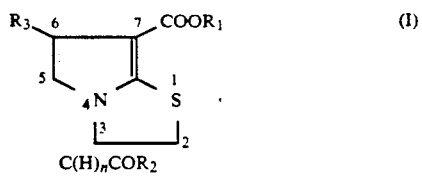

wherein $R_1$ represents a hydrogen atom, an alkyl group having from 1 to 10 carbon atoms or a cyclic alkyl group having from 3 to 8 carbon atoms;

$R_2$ represents a hydroxyl group, an alkoxy group which has an alkyl group having from 1 to 10 carbon atoms and which may have from one to three substituents selected from the group consisting of a halogen atom and a hydroxyl group in the alkyl group moiety, an arylthio group which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group in an aryl group moiety selected from the group consisting of phenyl, naphthyl, and biphenyl groups, an aryloxy group which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group in an aryl group moiety selected from the group consisting of phenyl, naphthyl, and biphenyl groups, an amino group, an alkylamino group or a cyclic amino group which is selected from the group consisting of azetidino, aziridino, pyrrolidino, imidazolidino, thiazolidino, oxazolidino, and pyrazolidino groups;

$R_3$ represents a hydrogen atom, an alkyl group having from 1 to 10 carbon atoms, an aryl group which is selected from the group consisting of phenyl, naphthyl, and biphenyl groups and which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group, or a heterocyclic group which is selected from the group consisting of furyl, thienyl, oxazolyl, imidazolyl, thiazolyl, and pyrrolyl groups and which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group;

n represents 1 or 2; and represents a single bond or a double bond; and pharmaceutically acceptable salts thereof.

2. A compound and pharmaceutically acceptable salts thereof as claimed in claim 1, wherein $R_1$ is a branched-chain alkyl group or a cyclic alkyl group, and $R_2$ is an alkylamino group or a cyclic amino group which is selected from the group consisting of azetidino, aziridino, pyrrolidino, imidazolidino, thiazolidino, oxazolidino, and pyrazolidino groups.

3. A compound and salts thereof as claimed in claim 1, wherein $R_1$ is an isopropyl group or a cyclohexyl group, $R_2$ is a methylamino group or an ethylamino group, $R_3$ is a methyl group or a hydrogen atom and the bond between the 5- and 6-positions is a double bond.

4. A compound and salts thereof as claimed in claim 1, wherein $R_1$ is a isopropyl group, $R_2$ is a methylamino group, $R_3$ is a methyl group and the bond between 5- and 6-positions is a double bond.

5. N-Methyl-(7-isopropoxycarbonyl-6-methyl-2,3-dihydropyrrolo[2,1-b]thiazol-3-ylidene)acetamide and pharmaceutically acceptable salts thereof as claimed in claim 1.

6. A pharmaceutical preparation for preventing or treating hepatic diseases which contains an effective amount of a compound represented by the following formula (I):

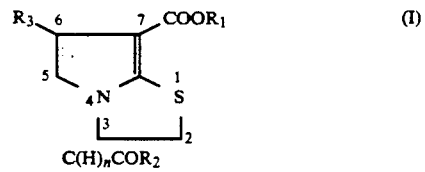

wherein $R_1$ represents a hydrogen atom, an alkyl group having from 1 to 10 carbon atoms or a cyclic alkyl group having from 3 to 8 carbon atoms;

$R_2$ represents a hydroxyl group, an alkoxy group which has an alkyl group having from 1 to 10 carbon atoms and which may have from one to three substituents selected from the group consisting of a halogen atom and a hydroxyl group in the alkyl group moiety, an arylthio group which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group in an aryl group moiety selected from the group consisting of phenyl, naphthyl, and biphenyl groups, an aryloxy group which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group in an aryl group moiety selected from the group consisting of phenyl, naphthyl, and biphenyl groups, an amino group, an alkylamino group or a cyclic amino group which is selected from the group consisting of azetidino, aziridino, pyrrolidino, imidazolidino, thiazolidino, oxazolidino, and pyrazolidino groups;

$R_3$ represents a hydrogen atom, an alkyl group having 1 to 10 carbon atoms, an aryl group which is selected from the group consisting of phenyl, naphthyl, and biphenyl groups and which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group, or a heterocyclic group which is selected from the group consisting of furyl, thienyl, oxazolyl, imidazolyl, thiazolyl, and pyrrolyl groups and which may have from one to three substituents selected from the group consisting of an alkyl group having from 1 to 10 carbon atoms, an alkoxy group which has an alkyl group having from 1 to 10 carbon atoms, a halogen atom, a hydroxyl group, an amino group, a carboxyl group, a nitro group, and a trifluoromethyl group;

n represents 1 or 2; and represents a single bond or a double bond; and pharmaceutically acceptable salts thereof as an active ingredient.

* * * * *